US00PP21377P2

(12) United States Plant Patent
Lyrene

(10) Patent No.: US PP21,377 P2
(45) Date of Patent: Oct. 12, 2010

(54) SOUTHERN HIGHBUSH BLUEBERRY PLANT NAMED 'FL03-291'

(50) Latin Name: ***Vaccinium corymbosum* L.**
Varietal Denomination: FL03-291

(75) Inventor: Paul M. Lyrene, Micanopy, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/584,568

(22) Filed: Sep. 8, 2009

(51) Int. Cl.
*A01H 5/00* (2006.01)

(52) U.S. Cl. ..... Plt./157

(58) Field of Classification Search ..... Plt./157
See application file for complete search history.

*Primary Examiner*—Susan B McCormick Ewoldt
(74) *Attorney, Agent, or Firm*—Jondle & Associates, P.C.

(57) ABSTRACT

'FL03-291' is a new southern highbush blueberry plant distinguished by a low chilling requirement with prolific early-spring leafing, a vigorous and upright to spreading growth habit, early ripening (50% ripe berries in north Florida by April 22) and berries that are sweet and firm with a small, dry picking scar, is disclosed.

2 Drawing Sheets

STATEMENT REGARDING FEDERALLY SPONSORED RESEARCH

Figure 1:
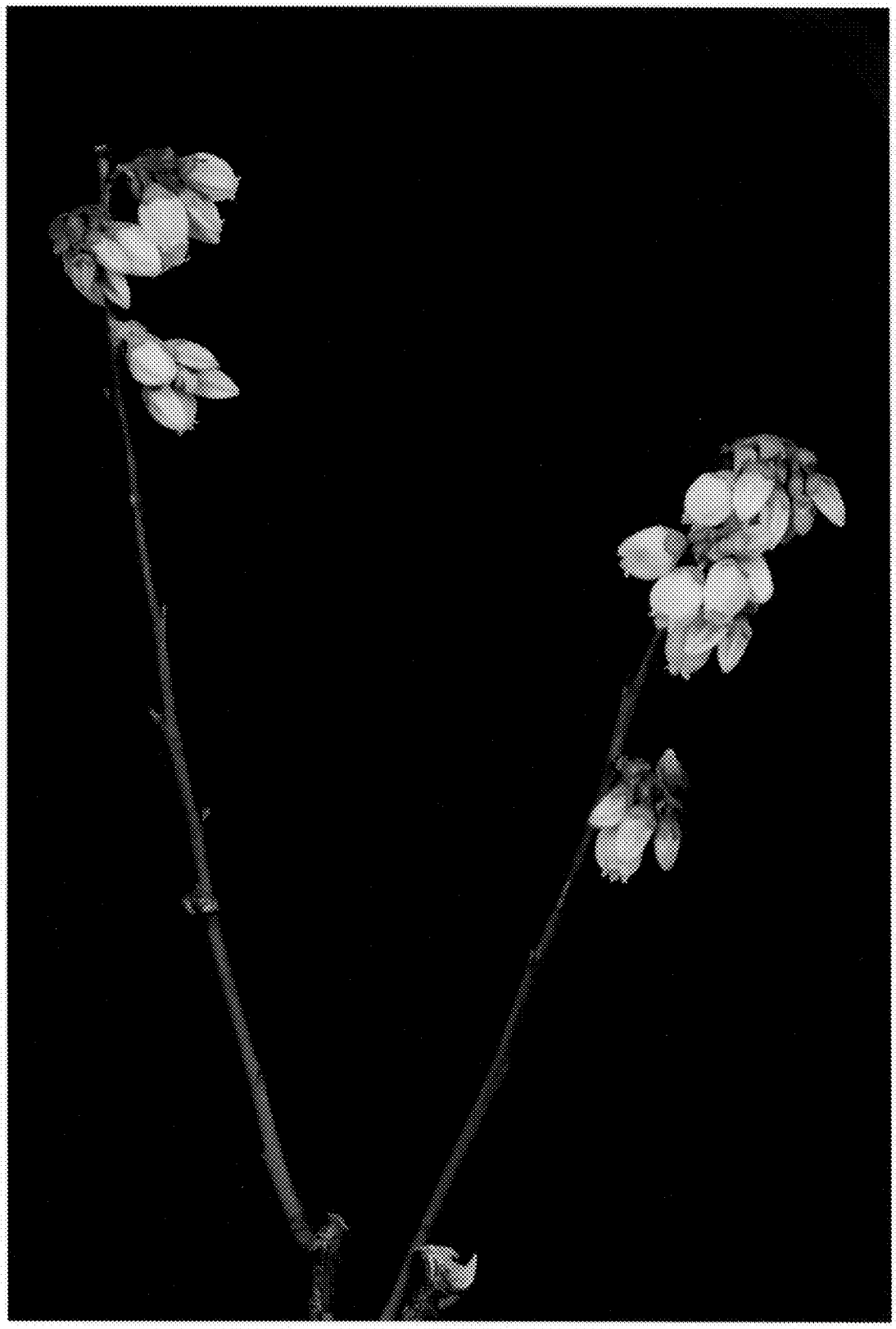

The present invention was supported in part by funds from the U.S. Government. The U.S. Government therefore may have certain rights in the invention.

Genus and species: *Vaccinium corymbosum* L.
Variety denomination: 'FL03-291'.

BACKGROUND OF THE INVENTION

The invention relates to a new and distinct variety of a southern highbush blueberry (*Vaccinium corymbosum* L.) hybrid named 'FL03-291'. 'FL03-291' is intended for production of fresh-market blueberries in early spring from areas with mild winters and early spring warmth. 'FL03-291' is a southern highbush blueberry clone distinguished by its low chilling requirement, its vigorous, disease-resistant bush, and by its firm, sweet berries that ripen from mid-April through early May when grown in north Florida. Approximately 100 plants of 'FL03-291' have been propagated by softwood cuttings at Gainesville, Fla., and have fruited for several years and the resulting plants have all been phenotypically indistinguishable from the original plant.

'FL03-291' originated as a seedling from the cross of the proprietary *Vaccinium corymbosum* L. female parent, 'FL00-28' (unpatented) with the proprietary *Vaccinium corymbosum* L. male parent, 'FL98-363' (unpatented) in a greenhouse in Gainesville, Fla. in February of 2000. The seedling was first fruited in a high-density field nursery in the spring of 2002. After the second year of fruiting in the field in the spring of 2002, the seedling was named 'FL03-291' and was propagated by softwood cuttings. An experimental 15-plant clonal plot was established in Windsor, Fla. in February of 2004. Based on the growth and berry characteristics of this plot, 'FL03-291' was re-propagated by softwood cuttings, and an experimental 30-plant clonal plot was established in Windsor in January of 2008.

'FL03-291' has been reproduced asexually for over seven years using softwood cuttings and has been found to retain its distinctive characteristics through successive asexual propagations.

Plant Breeder's Rights for this cultivar have not been applied for. 'FL03-291' has not been made publicly available more than one year prior to the filing date of this application.

SUMMARY OF THE INVENTION

The following are the most outstanding and distinguishing characteristics of 'FL03-291' when grown under normal horticultural practices in north Florida.

1. A low chilling requirement with prolific early-spring leafing;
2. A vigorous and upright to spreading growth habit;
3. Early ripening (50% ripe berries in north Florida by April 22); and
4. Berries that are sweet and firm with a small, dry picking scar.

DESCRIPTION OF THE PHOTOGRAPHS

This new southern highbush blueberry plant is illustrated by the accompanying photographs which show the plant's form, foliage, flower clusters and berry clusters. The colors shown are as true as can be reasonably obtained by conventional photographic procedures. The photographs were taken of the flowers in FIG. 1 were taken in February 2009 and the photographs of the berries in FIG. 2 and FIG. 3 were taken in April 2009 on 5-year-old plants, growing in a test field in North Florida.

FIG. 1 shows several clusters of opening flowers during the early stages of flowering in February. The flowers have a pink-rose color before anthesis, especially in bright sun with cool temperatures, but have become white by anthesis.

Figure 2:
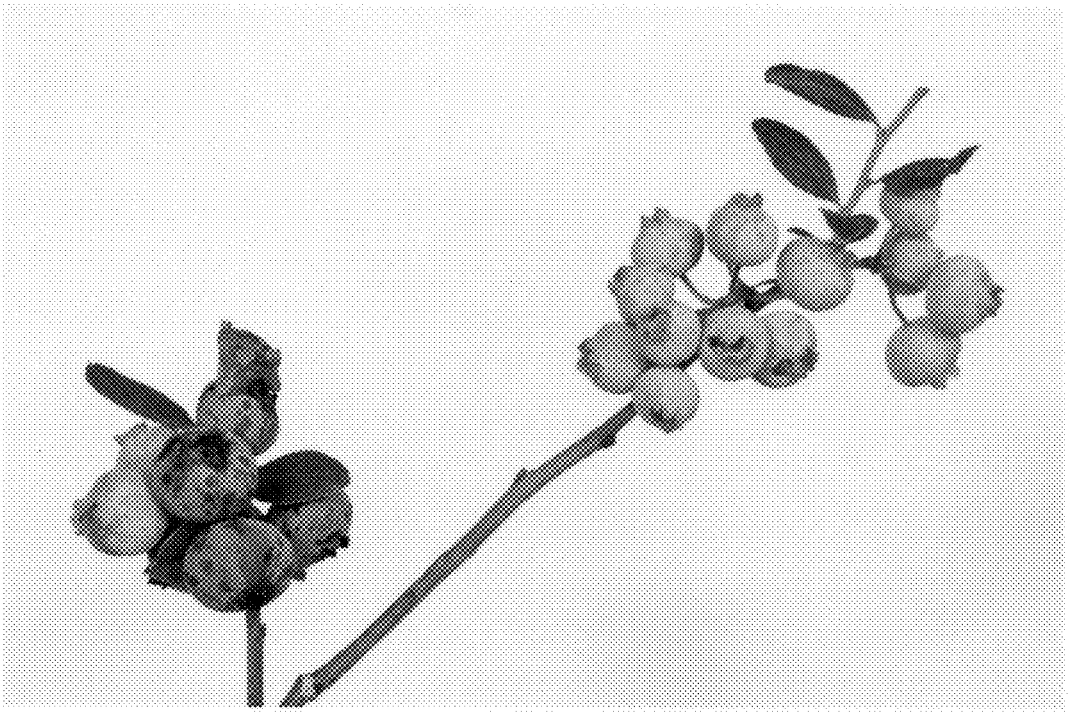

FIG. 2 shows several clusters of berries ripening in the field. The freckling pattern is due to naturally occurring minerals in the water being used in overhead irrigation of the plants and is not an inherent feature of the berries. The long pedicels produce a loose berry cluster.

Figure 3:
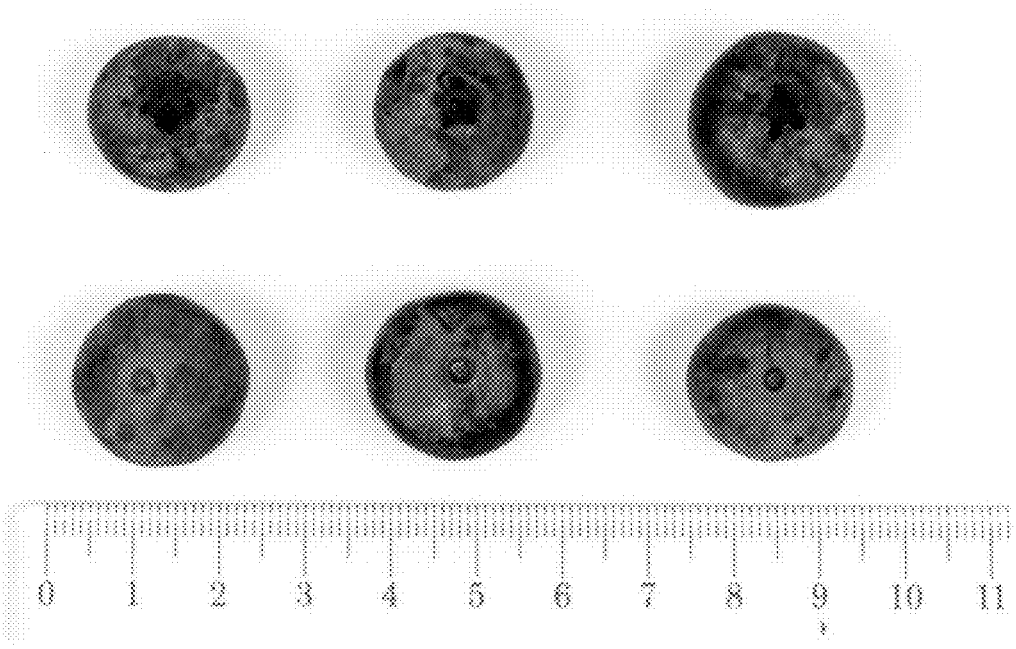

FIG. 3 shows the berries at close range. The small, dry picking scars and the calyx lobes, appressed to the berry surface and forming an irregular five-pointed star on some of the berries are visible.

DESCRIPTION OF THE NEW CULTIVAR

The following detailed description sets forth the distinctive characteristics of 'FL03-291'. The detailed description was taken on 5-year-old plants growing under field conditions near Windsor in northeast Florida. Data and descriptions were taken between February 1 and June 1, 2009 depending on the characteristics being evaluated. The color chart used in this specification is "The Pantone Book of Color", by Leatrice Eiseman and Lawrence Herbert (1990). Harry N. Abrams, Inc., Publishers, N.Y. Where colors in the drawings differ from the Pantone color designations in the verbal descriptions, the Pantone color designations are accurate.

DETAILED BOTANICAL DESCRIPTION

Classification:

*Botanical name: Vaccinium corymbosum* L.

*Common name.*—Southern highbush blueberry.

*Denomination.*—'FL03-291'.

Parentage:

*Female parent.*—'FL00-28' (unpatented).

*Male parent.*—'FL98-363' (unpatented).

Market class: 'FL03-291' produces southern highbush blueberries suitable for both the fresh and processed fruit markets.

Bush description:

*Plant height.*—2.5 m.

*Canopy diameter* (*measured at the widest part of the bush*).—3.0 m.

*Vigor.*—Very high.

*Growth habit.*—Between upright to spreading.

*Twigginess.*—Medium to high.

*Tendency toward evergreenness.*—Medium.

*Productivity.*—In northeast Florida, 'FL03-291' produces 5 to 8 pounds of berries per bush on plants 4-years-old or older.

*Chilling requirement.*—200 hours below 7° C.

*Cold hardiness.*—Flowers and fruit are hardy to −3° C.; the plant, during winter dormancy, is hardy to −15 C.

*Ease of propagation.*—Easy to propagate from softwood cuttings; the plants survive and grow well in nursery beds.

Trunks and branches:

*Suckering tendency.*—High; 5-year-old plants have an average of 10 major canes rising from near the base of the plant.

*Surface texture* (*of strong, 6-month-old shoots observed in June*).—Smooth.

*Surface texture* (*of 3-year-old and older wood*).—Rough due to exfoliation and production of vertical cracks.

*Color of 4-month-old twigs observed in June in the field.*—"Herbal Garden", Pantone 15-0336.

*Color of 3-year-old rough-textured canes.*—"White Swan", Pantone 12-0000.

*Internode length on strong, upright shoots measured in June.*—Averages about 2.0 cm.

Leaves:

*Length, mean* (*including petiole, from tip of petiole to end of blade*).—5.6 cm.

*Width, mean* (*at widest point*).—2.7 cm.

*Shape.*—Ovate, terminating in a very short dew tip, 0.03 cm long, which is visible with a 15X microscope.

*Margin.*—Entire.

*Color.*—Upper surface: "Chive", Pantone 19-0323. Lower surface: "Stone Green", Pantone 17-0123.

*Pubescence.*—Upper surface: Numerous short, white curled hairs on the midrib and principle lateral veins. Lower surface: Absent.

*Pubescence on margins.*—Absent.

*Relative time of leafing versus flowering.*—In commercial fields in north Florida, where the variety is sprayed with hydrogen cyanamide in midwinter, the variety begins to produce new leaves at the time of full bloom.

Flower:

*Arrangement.*—Flowers are arranged alternately along a short, leafless, deciduous branch.

*Fragrance.*—Slight rose.

*Shape.*—Urceolate.

*Flowering period.*—Mean date of 50% open flowers in Windsor, Florida is February 10 .

*Cluster habit.*—Very loose.

*Median number of flowers per cluster.*—4.

*Petals.*—Fused into a corolla with 5 lobes.

*Pedicel.*—Length at time of anthesis: 0.6 cm. Color: "Red Violet", Pantone 17-1818 on the side most exposed to sunlight.

*Peduncle.*—Length at time of anthesis: Highly variable; median is 0.8 cm. Color: "Red Violet", Pantone 17-1818 on the side most exposed to sunlight.

*Calyx.*—Diameter of calyx aperture on mature berry (longest diameter): 0.2 cm to 0.3 cm. Surface texture: Smooth. Color at anthesis: "Herbal Green", Pantone 15-0336.

*Corolla.*—Length (from pedicel attachment to corolla tip excluding the pedicel): 1.1 cm. Diameter of tube (at widest point): 0.7 cm. Aperture diameter: 0.2 cm to 0.3 cm. Surface texture: Smooth. Color at anthesis: White.

Reproductive organs:

*Style length* (*top of ovary to stigma tip*).—0.9 cm.

*Location of tip of stigma relative to lip of the corolla.*—The tip of the stigma ends approximately 1.0 mm below the tip of the corolla tube.

*Pollen.*—General: When the pollen is stained with 2% acetocarmine, the potential pollen fertility can be measured; 98% of the pollen tetrads appear normal and are stained. Abundance of shed: High. Color of dried pollen: "Winter White", Pantone 11-0507.

Self-fruitfulness: Low to medium; planting in field configurations that promote cross pollination with other southern highbush clones is recommended for all southern highbush in Florida.

Fruit:

*Mean date of first commercial harvest* (25% *of berries ripe*).—April 16.

*Mean date of mid-harvest.*—April 22.

*Mean date of last harvest.*—May 5.

*Diameter of calyx aperture on mature berry.*—0.2 cm to 0.3 cm.

*Size and shape of calyx lobes on mature berry.*—Appressed to the berry surface; on some berries, they form an irregular 5-pointed star shape.

*Pedicel length on ripe berry.*—Median is 0.5 cm.

*Peduncle length on ripe berry.*—Variable; median is 0.8 cm.

*Detachment force for ripe berries.*—Very low.

*Number of berries per cluster.*—5.

Berry:

*Cluster habit.*—Loose.

*Weight* (*on well-pruned plants*).—2.7 g per berry.

*Height.*—1.45 cm.

*Width.*—1.85 cm.

*Shape.*—Subglobose; the polar diameter is shorter than the equatorial diameter.

*Surface color of immature berries, with bloom.*—The side exposed to the sun has a blush that is "Pearl", Pantone 12-1304; the background color is "Murmur", Pantone 12-5203.

*Surface color of mature berries while on the plant.*—"Gray Dawn", Pantone 14-4106.

*Surface color of ripe berry after polishing.*—Shiny black.

*Surface wax.*—Medium to slightly below normal in amount and in persistence during handling of the berry.

*Pedicel scar.*—Small and dry.

*Firmness.*—High.

*Flavor.*—Sweet, low acidity.

*Texture.*—Good; small seeds, thin skin.

Seeds:

*Color of dried seeds.*—"Rawhide", Pantone 18-1137.

*Weight of well-developed dried seed.*—0.8 mg per seed.

*Length of well-developed dried seed.*—0.15 cm.

Disease and insect resistance: 'FL03-291' has grown vigorously and shows good bush survival in the field. It appears to have above-average resistance to root rot (*Phytophthora cinnamomi*) and stem blight (*Botryosphaeria dothidia*). The plants have shown no signs of cane canker (*Botryosphaeria corticis*) susceptibility in the field. The fungal leaf spots that are common on highbush blueberries grown in Florida are easily controlled by approved fungicides.

COMPARISON WITH PARENTAL LINES AND KNOWN CULTIVARS

'FL03-291' is distinguished from the proprietary *Vaccinium corymbosum* L. female parent, 'FL00-28' (unpatented) in that 'FL03-291' has a more vigorous growth habit, lighter colored berries and a better picking scar than 'FL00-28'.

'FL03-291' is distinguished from the proprietary *Vaccinium corymbosum* L. male parent, 'FL98-363' (unpatented) in that 'FL03-291' has a more upright plant habit and a larger berry than 'FL98-363'.

'FL03-291' is distinguished from the comparison commercial variety 'Farthing' (U.S. Plant Pat. No. 19,341) in that 'FL03-291' has elliptic-shaped leaves, a loose flower cluster and an average of 4 flowers per cluster, while 'Farthing' has ovate-shaped leaves, a medium flower cluster and an average of 6 to 7 flowers per cluster.

'FL03-291' is distinguished from the comparison commercial variety 'Star' (U.S. Plant Pat. No. 10,675) in that 'FL03-291' has a more vigorous growth habit and flowers approximately 3 days earlier than 'Star'. 'FL03-291' has larger berries (2.7 g) than 'Star' (2.0 g). Additionally, 'FL03-291' is more resistant to cane canker disease (caused by *Botryosphaeria corticis*) than 'Star'.

I claim:

1. A new and distinct cultivar of southern highbush blueberry plant as shown and described herein.

* * * * *